(12) United States Patent
Dryga et al.

(10) Patent No.: US 12,320,795 B2
(45) Date of Patent: Jun. 3, 2025

(54) MEASUREMENT SYSTEMS AND ASSOCIATED TECHNIQUES FOR SENSING ELECTRICAL CHARACTERISTICS OF A SENSOR

(71) Applicant: NanoDX, Inc., Southborough, MA (US)

(72) Inventors: Sergey A. Dryga, Rio Rancho, NM (US); Jonathon D. McMillan, Tijeras, NM (US)

(73) Assignee: NanoDX, Inc., Southborough, MA (US)

( * ) Notice: Subject to any disclaimer, the term of this patent is extended or adjusted under 35 U.S.C. 154(b) by 0 days.

(21) Appl. No.: 17/203,425

(22) Filed: Mar. 16, 2021

(65) Prior Publication Data

US 2021/0293776 A1    Sep. 23, 2021

Related U.S. Application Data

(60) Provisional application No. 62/991,515, filed on Mar. 18, 2020.

(51) Int. Cl.
*G01N 33/48*    (2006.01)
*G01N 27/414*   (2006.01)
(Continued)

(52) U.S. Cl.
CPC ... *G01N 33/48707* (2013.01); *G01N 27/4146* (2013.01); *G01N 27/60* (2013.01); *G01R 27/14* (2013.01)

(58) Field of Classification Search
CPC ......... G01N 33/48707; G01N 27/4146; G01N 27/60; G01R 27/14; G01R 27/02
See application file for complete search history.

(56) References Cited

U.S. PATENT DOCUMENTS 4,649,736 A * 3/1987 Austin ................. G01N 27/121
                                                        73/25.05
8,323,466 B2   12/2012 Kim et al.
(Continued)

FOREIGN PATENT DOCUMENTS

EP    0390721 A1 * 10/1990 ............ G01P 15/125
EP    2714935 B1 *  3/2017 ........ B01L 3/502715
(Continued)

OTHER PUBLICATIONS

International Search Report and Written Opinion for International Application No. PCT/US2021/022539 mailed Jun. 25, 2021.
(Continued)

*Primary Examiner* — Catherine T. Rastovski
*Assistant Examiner* — Lal C Mang
(74) *Attorney, Agent, or Firm* — Wolf, Greenfield & Sacks, P.C.

(57) ABSTRACT

Systems, devices, and methods of sensing electrical characteristics of a sensor are generally provided. Measurement devices described herein employ techniques for improved sensitivity when sensing electrical characteristics of a sensor. In some aspects, measurement devices described herein may be configured to reduce the impact of current noise generated in components of a measurement system when sensing electrical characteristics of the sensor. The techniques described herein may facilitate the inclusion of larger sense resistors in measurement devices, which increases the sensitivity of the system. In some aspects, such techniques may also facilitate coupling the sensor between the measurement device and ground when sensing the electrical characteristics for improved protection against overvoltage events such as electrostatic discharge (ESD).

23 Claims, 9 Drawing Sheets

(51) Int. Cl.
  *G01N 27/60* (2006.01)
  *G01N 33/487* (2006.01)
  *G01R 27/14* (2006.01)

(56) References Cited

U.S. PATENT DOCUMENTS

| | | | |
|---|---|---|---|
| 9,628,195 | B2 | 4/2017 | Jiang et al. |
| 9,983,163 | B2 | 5/2018 | Hassibi et al. |
| 10,288,678 | B2 | 5/2019 | Warnock |
| 2004/0210289 | A1* | 10/2004 | Wang ............... A61N 1/05 607/116 |
| 2014/0093897 | A1 | 4/2014 | Szeto et al. |
| 2016/0290958 | A1 | 10/2016 | Ram et al. |
| 2017/0145481 | A1* | 5/2017 | Kim ................ C12Q 1/6809 |
| 2017/0207760 | A1* | 7/2017 | Werking ......... H03F 3/45475 |
| 2018/0059054 | A1 | 3/2018 | Nishida |
| 2018/0323750 | A1* | 11/2018 | Wang ............... H03F 1/26 |
| 2019/0137431 | A1 | 5/2019 | Yanagawa et al. |
| 2019/0310221 | A1* | 10/2019 | Marquant ......... G01N 27/3274 |
| 2021/0190711 | A1 | 6/2021 | Khosravi et al. |
| 2021/0190723 | A1 | 6/2021 | Khosravi et al. |

FOREIGN PATENT DOCUMENTS

| | | | |
|---|---|---|---|
| JP | 2010-136169 A | 6/2010 | |
| JP | 2010-230525 A | 10/2010 | |
| WO | WO-2019173220 A1 * | 9/2019 | ............... A61B 1/05 |

OTHER PUBLICATIONS

Vergani et al., Multichannel bipotentiostat integrated with a microfluidic platform for electrochemical real-time monitoring of cell cultures. IEEE Trans Biomed Circuits Syst. Oct. 2012;6(5):498-507. doi: 10.1109/TBCAS.2012.2187783.

Yencha et al., Design of an Addressable Internetworked Microscale Sensor. JSAM. Dec. 2010: 7 pages.

* cited by examiner

MEASUREMENT SYSTEMS AND ASSOCIATED TECHNIQUES FOR SENSING ELECTRICAL CHARACTERISTICS OF A SENSOR

RELATED APPLICATIONS

This application claims priority under 35 U.S.C. § 119 (e) to U.S. Provisional Application No. 62/991,515, filed Mar. 18, 2020, and entitled "Measurement Systems and Associated Techniques for Sensing Electrical Characteristics of a Sensor," which is incorporated herein by reference in its entirety.

FIELD

The present application relates generally to systems, devices, and methods for sensing electrical characteristics of one or more sensors, and, more particularly, to systems, devices, and methods suitable for sensing electrical characteristics to detect features of bodily fluids.

BACKGROUND

Sensors may be employed to detect one or more features of bodily fluids. One manner in which features may be detected is using measurement circuitry coupled to the sensors, which may sense electrical characteristics of the sensors. However, some sensors have undesirably low sensitivity to analytes of interest, which can result in signals being provided to the measurement circuitry that are too weak to be useful for detecting features. Accordingly, improved measurement circuitry is needed.

SUMMARY

Sensors, related components, and related methods are generally described.

Some embodiments of the present disclosure relate to a device for sensing electrical characteristics of a sensor. The device may comprise a sense resistor configured for coupling to the sensor, a first amplifier having a first input, a second input, and an output, with the sense resistor coupled between the second input and the output, and a second amplifier comprising a first input coupled to the output of the first amplifier, a second input coupled to the first input of the first amplifier, and an output configured to provide a voltage indicative of the electrical characteristics of the sensor.

In some embodiments, the electrical characteristics may include a conductance of the sensor.

In some embodiments, the sensor may comprise a nanowire sensor.

In some embodiments, the device may further comprise the nanowire sensor, and the nanowire sensor may be configured such that the conductance indicates a presence of one or more analytes at a surface of the nanowire sensor.

In some embodiments, the surface of the nanowire sensor may comprise a binding entity for a biomarker for brain injury.

In some embodiments, the surface of the nanowire sensor may comprise a binding entity for a biomarker, the biomarker selected from a group comprising GFAP, UCH-L1, S100β, ICH, and NFL-1.

In some embodiments, the surface of the nanowire sensor may comprise a binding entity for a biomarker for one or more infectious disease agents.

In some embodiments, the surface of the nanowire sensor may comprise a binding entity for a biomarker for sepsis.

In some embodiments, the device may further comprise a transimpedance amplifier (TIA) including the sense resistor and the first amplifier, and the TIA may be configured to generate a sense voltage indicative of a current flowing through the sensor.

In some embodiments, the second amplifier may comprise at least one member of a group comprising an instrumentation amplifier, a difference amplifier, and an operational amplifier.

In some embodiments, the TIA may be contained in a single integrated circuit package.

In some embodiments, the TIA may comprise a plurality of discrete components.

In some embodiments, the plurality of discrete components may comprise a field-effect transistor (FET).

Some embodiments of the present disclosure relate to a system comprising a printed circuit board (PCB) having the device and at least one electrical connector mounted thereon, and the electrical connector may be configured for electrically coupling the device to the sensor.

In some embodiments, the electrical connector may be configured for removably coupling the device to the sensor.

Some embodiments of the present disclosure relate to a device for sensing electrical characteristics of a sensor. The device may comprise a sense amplifier comprising a first input and an output, the sense amplifier configured to generate a voltage indicative of the electrical characteristics at the output, and a transimpedance amplifier (TIA), comprising a first input coupled to the first input of the sense amplifier and a second input configured for coupling to the sensor.

In some embodiments, the electrical characteristics include a conductance of the sensor.

In some embodiments, the sensor may comprise a nanowire sensor.

In some embodiments, the device may further comprise the nanowire sensor, and the nanowire sensor may be configured such that the conductance indicates a presence of one or more analytes at a surface of the nanowire sensor.

In some embodiments, the surface of the nanowire sensor may comprise a binding entity for a biomarker.

In some embodiments, the biomarker may be a biomarker for brain injury.

In some embodiments, the surface of the nanowire sensor may comprise a binding entity for a biomarker, the biomarker selected from a group comprising GFAP, UCH-L1, S100β, ICH, and NFL-1.

In some embodiments, the biomarker may be a biomarker for one or more infectious disease agents.

In some embodiments, the biomarker may be for sepsis.

In some embodiments, the TIA may further comprise an output electrically coupled to a second input of the sense amplifier, and the TIA may be configured to generate a sense voltage at the output of the TIA that is indicative of a current through the sensor.

In some embodiments, the TIA may be further configured to receive an input voltage signal at the first input of the TIA and to apply the input voltage signal to the sensor via the second input of the TIA.

In some embodiments, the TIA may further comprise a sense resistor electrically coupled between the first input of the TIA and the output of the TIA and configured to generate the sense voltage when the current flows through the sense resistor.

In some embodiments, the sense amplifier may comprise at least one member of a group comprising an instrumentation amplifier, a difference amplifier, and an operational amplifier.

Some embodiments of the present disclosure relate to a system comprising a printed circuit board (PCB) having the device and at least one electrical connector mounted thereon, and the electrical connector may be configured for electrically coupling to the sensor.

In some embodiments, the electrical connector may be configured for removably coupling to the sensor.

Some embodiments of the present disclosure relate to a system for sensing electrical characteristics of a sensor. The system may comprise a transimpedance amplifier (TIA) configured to provide an alternating current (AC) voltage to the sensor and a sense amplifier configured to generate a voltage indicative of the electrical characteristics responsive to detecting a current flowing between the sensor and ground.

In some embodiments, the TIA may be configured to receive the AC voltage from an AC voltage source having a frequency between 0.1 Hz and 1 kHz.

In some embodiments, the TIA may be configured to receive the AC voltage from an AC voltage source having a frequency between 500 Hz and 700 Hz.

In some embodiments, the TIA may be configured to receive the AC voltage from an AC voltage source having a frequency of 600 Hz.

In some embodiments, the electrical characteristics may include a conductance of the sensor.

In some embodiments, the sensor may comprise a nanowire sensor.

In some embodiments, the system may further comprise the nanowire sensor, and the nanowire sensor may be configured such that the conductance indicates a presence of one or more analytes at a surface of the nanowire sensor.

In some embodiments, the nanowire sensor may be configured to generate an impedance greater than 0.5 M$\Omega$ when at least some analytes are disposed at the surface of the nanowire sensor.

In some embodiments, the nanowire sensor may be configured to generate an impedance greater than 50 M$\Omega$ when at least some analytes are disposed at the surface of the nanowire sensor.

In some embodiments, the nanowire sensor may be configured to generate an impedance greater than 75 M$\Omega$ when at least some analytes are disposed at the surface of the nanowire sensor.

In some embodiments, the nanowire sensor may be configured to generate an impedance greater than 100 M$\Omega$ when at least some analytes are disposed at the surface of the nanowire sensor.

In some embodiments, the surface of the nanowire sensor may comprise a binding entity for a biomarker.

In some embodiments, the biomarker may be a biomarker for brain injury.

In some embodiments, the surface of the nanowire sensor may comprise a binding entity for a biomarker, the biomarker selected from a group comprising GFAP, UCH-L1, S100$\beta$, ICH, and NFL-1.

In some embodiments, the biomarker may be a biomarker for one or more infectious disease agents.

In some embodiments, the biomarker may be a biomarker for sepsis.

In some embodiments, an input of the TIA may be configured to receive the current and an output of the TIA may be configured to provide a sense voltage to the sense amplifier.

In some embodiments, the TIA may further comprise a sense resistor configured to generate the sense voltage when the current flows through the sense resistor.

In some embodiments, the sense amplifier may comprise at least one member of a group comprising an instrumentation amplifier, a difference amplifier, and an operational amplifier.

In some embodiments, the system may further comprise a printed circuit board (PCB) having the TIA, sense amplifier, and at least one electrical connector mounted thereon, and the electrical connector may be configured for electrically coupling to the sensor.

Other advantages and features of the present application will become apparent from the following detailed description of various non-limiting embodiments of the application when considered in conjunction with the accompanying figures. In cases where the present application and a document incorporated by reference include conflicting and/or inconsistent disclosure, the present application shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the application shown where illustration is not necessary to allow those of ordinary skill in the art to understand the invention. In the figures.

DETAILED DESCRIPTION

Figure 1:
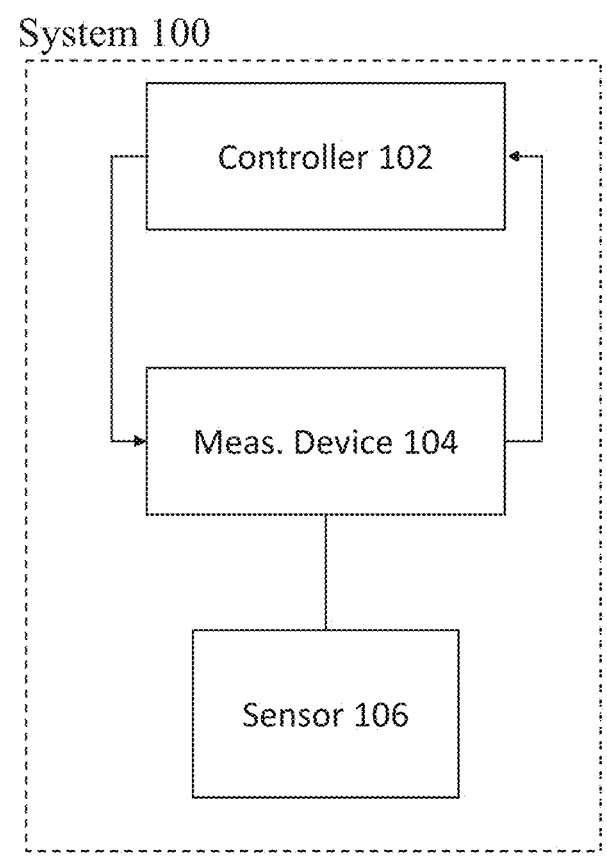
FIG. 1 shows an exemplary system for sensing electrical characteristics of a sensor, in accordance with some embodiments.

Systems, devices, and methods of sensing electrical characteristics of a sensor are generally provided. Measurement devices described herein may be configured for improved sensitivity when sensing electrical characteristics of a sensor.

In some aspects, a sensor described herein may be configured to generate signals indicative of the environment of the sensor when a bias signal (e.g., voltage) is applied to the sensor. For instance, the signals may indicate electrical characteristics of the sensor. In one example, a nanowire sensor may generate a current when a bias voltage is applied to the nanowire sensor such that the current indicates an impedance of the nanowire sensor that may vary according to the environment of the nanowire sensor. When such a sensor is disposed proximate bodily fluids, the impedance of the sensor may indicate the presence of one or more analytes in the bodily fluids proximate the sensor. Exemplary applications for sensing systems described herein include detecting biomarkers for an illness, condition, or injury, such as traumatic brain injury. For instance, one or more surfaces of the nanowire sensor may have a binding entity for a biomarker thereon, such as joined to the surface(s) by covalent bond, non-covalent bond, and/or the like, as described in more detail below.

However, signals from such sensors are typically very small (e.g., between 10 pico-amps (pA) and 1 micro-amp (µA)), such that a very sensitive measurement system is needed for the data from the sensor to be useable. For instance, if a system has inadequate sensitivity to sensed signals, interference from noise, distortion, and/or other factors may overwhelm the sensed signals, rendering the signals indiscernible over the interference. Accordingly, it is desirable to increase the sensitivity of such measurement systems to detect even very small signals.

Challenges arise in improving the sensitivity of a measurement system. For instance, when sensing a very small current, one way to increase the sensitivity of measurement devices in the system is to employ a large sense resistor to generate a large sense voltage indicative of the sensed current. However, large sense resistors also generate voltage when current noise generated in the system enters the sense path and adds to the sensed current. As a result, much of the sense voltage generated in the sense resistor corresponds to noise rather than signal. In some applications, the added noise defeats the increase in sensitivity provided by the large sense resistor. A similar problem arises when the sensor is biased using alternating current (AC) signals, as parasitic capacitances in the measurement system create non-linear impedances in the sense path, adding distortion to the sense voltage that impacts the ability of the system to determine the electrical characteristics.

In some aspects described herein, the inventors developed techniques for implementing measurement devices that reduce the impact of current noise and distortion generated by components of a measurement system when sensing electrical characteristics of a sensor. In some embodiments, a device for sensing electrical characteristics of a sensor may include first and second amplifiers, the second amplifier having inputs respectively coupled to an input and an output of the first amplifier. A sense resistor may be coupled between a second input and an output of the first amplifier, and an output of the second amplifier may be configured to provide a voltage indicative of the electrical characteristics of the sensor. In some embodiments, a device for sensing electrical characteristics of a sensor may include a sense amplifier configured to generate a voltage indicative of the electrical characteristics at its output, and a transimpedance amplifier (TIA) having a first input coupled to an input of the sense amplifier and a second input configured for coupling to the sensor. The inventors recognized that such amplifier interconnection configurations reduce the impact of current noise in the system, such as by limiting the amount of current noise to which the sensing path is exposed. The configurations also facilitate the inclusion of larger sense resistors in measurement devices, which increases the sensitivity of the system.

Techniques described herein may also facilitate using alternating current (AC) bias signals for sensing, as the impact of distortion on the AC signals is reduced. In some embodiments, a system for sensing electrical characteristics of a sensor may include a TIA configured to provide an alternating current (AC) voltage to the sensor and a sense amplifier configured to generate a voltage indicative of the electrical characteristics responsive to detecting a current flowing between the sensor and ground. Moreover, techniques described herein may also facilitate coupling a sensor between the measurement device and ground for improved protection against overvoltage events such as electrostatic discharge (ESD), as the sensor may be configured to dissipate ESD energy to ground, limiting the impact of an ESD event.

Turning to the figures, FIG. 1 shows an exemplary system 100 for sensing electrical characteristics of a sensor, in accordance with some embodiments. In FIG. 1, system 100 includes controller 102, measurement device 104, and sensor 106, which are shown electrically interconnected. In some embodiments, sensor 106 may be positioned in the vicinity of one or more bodily fluids, and electrical characteristics of sensor 106 may change depending on one or more features of the bodily fluid(s). For instance, the electrical characteristics may include an impedance (and/or admittance, conductance, etc.) of sensor 106. In one example, the impedance of sensor 106 may indicate the presence of one or more analytes proximate the sensor 106. For instance, sensor 106 may include a nanowire sensor having a binding entity for a biomarker thereon. Measurement device 104 may be configured to sense the electrical characteristics of sensor 106 and provide an indication of the electrical characteristics to controller 102. In the above example, controller 102 may be configured to analyze the electrical characteristics to determine the presence of the analyte(s).

In some embodiments, controller 102 may include bias circuitry configured to provide one or more bias signals (e.g., voltages and/or currents) to measurement device 104, and measurement device 104 may be configured to apply the bias signal(s) (e.g., directly or indirectly) to sensor 106, and to sense the electrical characteristics of sensor 106 responsive to applying the bias signal(s) to sensor 106. For instance, to determine an impedance of sensor 106, measurement device 104 may apply a voltage across sensor 106 and sense a current passing through sensor 106. Measurement device 104 may be further configured to provide an indication of the sensed electrical characteristics to controller 102 for analysis. For instance, measurement device 104 may provide a signal to controller 102 representative of the current passing through sensor 106, which indicates the impedance of sensor 106. In this example, controller 102 may determine the impedance of sensor 106 using Ohm's law, and controller 102 may also determine whether or how many analytes are proximate sensor 106 based on the impedance.

It should be appreciated that, in some embodiments, measurement device 104 may be configured to generate a voltage and/or current based on the bias signal(s) from controller 102 and provide the generated voltage and/or current to sensor 106 rather than the bias signal(s). It should further be appreciated that, in some embodiments, system 100 may include a first controller configured to provide the bias signal(s) and a second controlled configured to receive and process the indication of sensed electrical characteristics from measurement device 104.

In some embodiments, controller 102, measurement device 104, and sensor 106 may be packaged together, such as being positioned on a same circuit board (e.g., printed circuit board) and/or within a same housing. Alternatively, in some embodiments, controller 102 and/or measurement device 104 may be packaged separately from sensor 106. For example, controller 102 and measurement device 104 may be disposed on a first circuit board and/or contained in a first integrated circuit package, and sensor 106 may be disposed on a second circuit board and/or contained in a second integrated circuit package. For instance, in this example, the circuit board having controller 102 and measurement device 104 thereon may include an electrical connector configured to receive a complementary electrical connector to electrically couple measurement device 104 and/or controller 102 to sensor 106.

Figure 2:
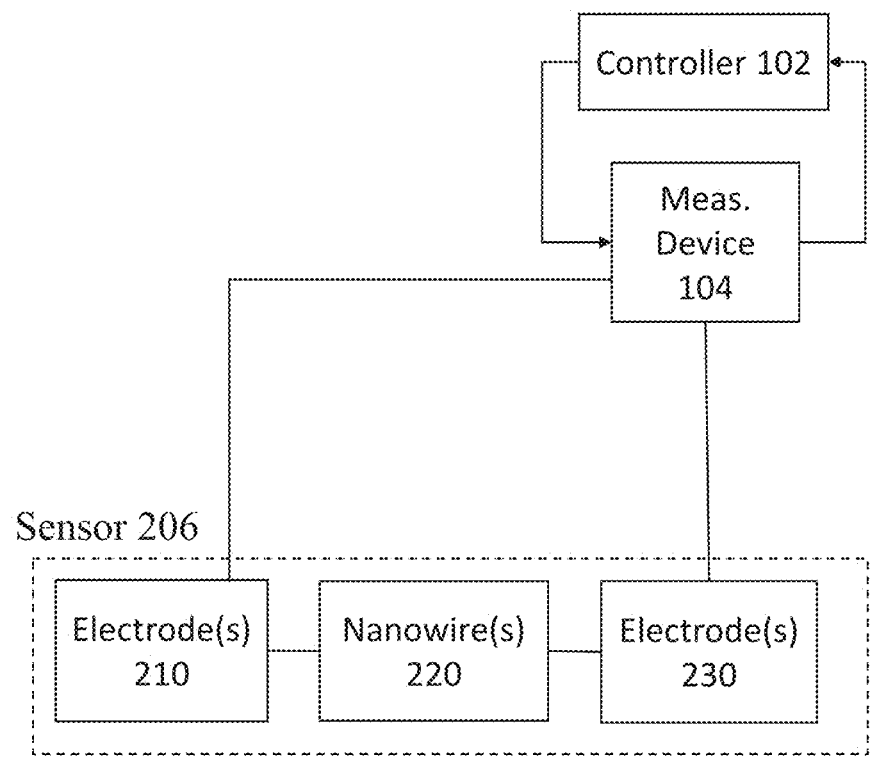
FIG. 2 shows an exemplary sensor that may be included in the system of FIG. 1, in accordance with some embodiments.

FIG. 2 shows an exemplary nanowire sensor 206 that may be included in system 100, in accordance with some embodiments. Sensor 206 is shown including electrodes 210 and 230 coupled to terminals of nanowires 220. Accordingly, when a voltage is applied to electrodes 210 and 230, the voltage is applied across the terminals of nanowires 220. For instance, the voltage may be provided by measurement device 104 in the manner described in connection with FIG. 1. In accordance with various embodiments, the applied signal may include a DC voltage and/or current and/or an AC voltage and/or current.

In some embodiments, one of the terminals of sensor 206 may be coupled to ground, such as a DC ground reference from which the DC voltage and/or AC voltage are referenced, and/or a DC voltage reference about which an AC signal applied to the other terminal operates. The inventors recognized that grounding a terminal of sensor 206 provides improved protection against overvoltage events such as ESD events. For instance, grounding a terminal of sensor 206 may provide a dissipation path for ESD charge, thus preventing a buildup of high voltage (e.g., on the order of kilo-volts (kV)) and reducing the impact of an ESD event.

In some embodiments, nanowires 220 of sensor 206 may be positioned in the vicinity of one or more bodily fluids, such that the presence or absence of analytes in the fluid(s) affects the impedance of nanowires 220. For instance, the presence of analytes may decrease the impedance of nanowires 220. As a result, nanowires 220 may conduct a higher current between electrodes 210 and 230 when a greater number of analytes are proximate nanowires 220 than when a lesser number of analytes are present. In some embodiments, nanowire sensor 206 may be configured to generate an impedance greater than 0.5 M Ω when at least some analytes are disposed at a surface of nanowire sensor 206. In some embodiments, nanowire sensor 206 may be configured to generate an impedance greater than 50 M Ω when at least some analytes are disposed at a surface of nanowire sensor 206. In some embodiments, nanowire sensor 206 may be configured to generate an impedance greater than 75 M Ω when at least some analytes are disposed at a surface of nanowire sensor 206. In some embodiments, nanowire sensor 206 may be configured to generate an impedance greater than 100 M Ω when at least some analytes are disposed at a surface of nanowire sensor 206.

In some embodiments, one or more surfaces of nanowires 220 may include a binding entity for a biomarker. For example, the binding entity may be joined by a covalent bond to a surface of nanowires 220. Alternatively, the binding entity may be joined to the surface by a non-covalent association and/or affinity such as a non-covalent bond (e.g., by adsorption). In some applications, the biomarker may be associated with traumatic brain injury. In some such embodiments, the nanowires may comprise a binding entity for a biomarker for brain injury. In accordance with various embodiments, the biomarker may be glial fibrillary acidic protein (GFAP), UCH-L1, S100β, ICH, or NFL-1, a small molecule and/or a lipid. Accordingly, one or more binding entities, for one or more of GFAP, UCH-L1, S100β, ICH, NFL-1 and/or other suitable biomarker, may be present on a surface of the nanowires. In some embodiments, multiple binding entities to one or more biomarkers may be bonded to one or more surfaces of nanowires 220, and/or to surfaces of multiple nanowires of a same or multiple sensors in a measurement system. For example, in one set of embodiments, a first nanowire or set of nanowires comprises a first binding entity for one of GFAP, UCH-L1, S100β, ICH, NFL-1, and second nanowire or set of nanowires comprises a second binding entity for one of GFAP, UCH-L1, S100β, ICH, NFL-1. In some embodiments, the first and second binding entities are different, and may bind to different biomarkers. Other configurations are also possible. Examples of binding, binding entities, biomarkers, and other components are provided in U.S. Application No. 62/953,140 filed Dec. 23, 2019, entitled Sensor System and Methods, which is incorporated herein by reference in its entirety for all purposes.

In some embodiments, sensors and/or nanowires described herein may include one or more binding entities for biomarkers other than those associated with brain injury. For example, such binding entities and/or biomarkers may include biomarkers associated with infectious disease agents, sepsis biomarkers, or any other suitable biomarker.

The sensors described herein may be suitable for sensing a variety of analytes in a variety of fluids. In some embodiments, the fluid is a bodily fluid. The sensor may be suitable for sensing an analyte in a human bodily fluid of a human and/or in a non-human, animal bodily fluid. Non-limiting types of suitable bodily fluids include types of blood (e.g., venous whole blood, capillary whole blood), components of blood (e.g., plasma, serum), urine, saliva, tears, and/or cerebro-spinal fluid. The bodily fluid may be obtained by, e.g., a finger stick. In some embodiments, the bodily fluid may include a throat or nasal swab incubated in a buffer solution, with at least some throat or nasal mucus transferred into the buffer solution.

In some embodiments, a sensor described herein may sense an analyte in a fluid via an electrostatic interaction. By way of example, a charged analyte may experience electrostatic attraction to a nanowire and/or a blocking layer disposed thereon. This electrostatic attraction may cause the analyte to deposit on the nanowire and/or blocking layer. In some embodiments, the analyte is a charged molecule, such as a charged biological polymer and/or a charged biological small molecule. Non-limiting examples of suitable analytes (e.g., charged analytes) include proteins (e.g., GFAP, UCH-L1, S100β, ICH, NFL-1), peptides, nucleic acids (e.g., DNA, RNA, PNA), lipids, carbohydrates, small molecules, and derivatives of the foregoing.

When electrical characteristics of the sensor are sensed, a constant voltage may be applied (e.g., by measurement device 104) across electrodes 210 and 230, such that changes in the current through nanowires 220 depend predominantly on whether or how many analytes are proximate nanowires 220. Measurement device 104 may be configured to sense the current through nanowires 220 and provide an indication of the current to controller 102, such as described in connection with FIG. 1.

Figure 6:
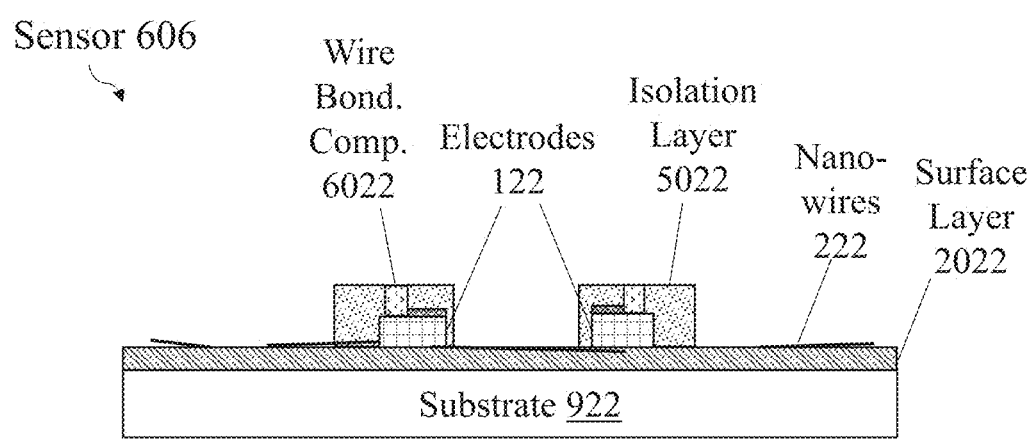
FIG. 6 shows one example of a sensor comprising a wire bonding composition disposed on a portion of each member of the pair of electrodes, in accordance with some embodiments.
Figure 7:
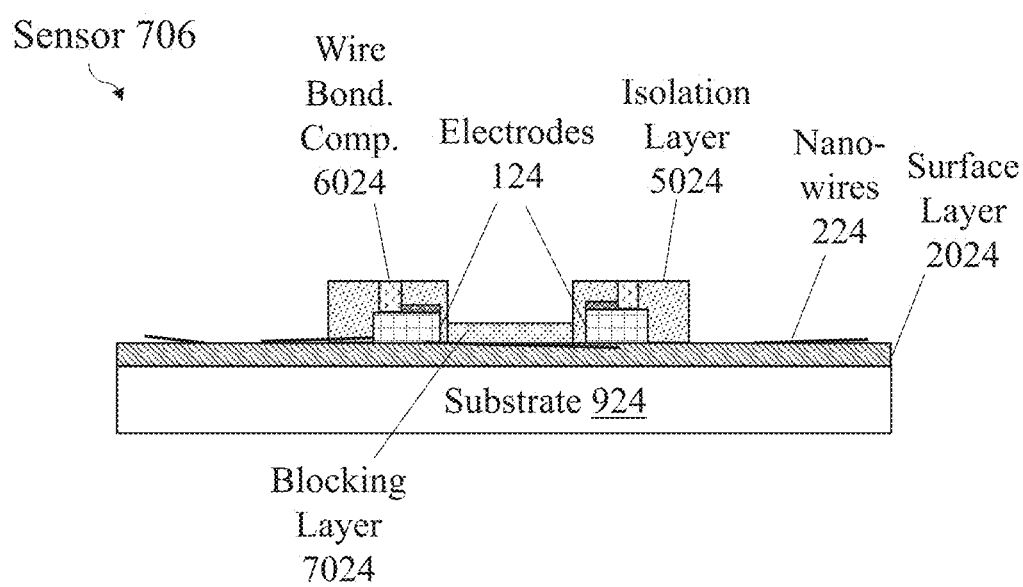
FIG. 7 shows one example of a sensor comprising a blocking layer that is disposed over a nanowire placing a pair of electrodes in electrical communication, but absent from other portions of the sensor, in accordance with some embodiments.
Figure 8:
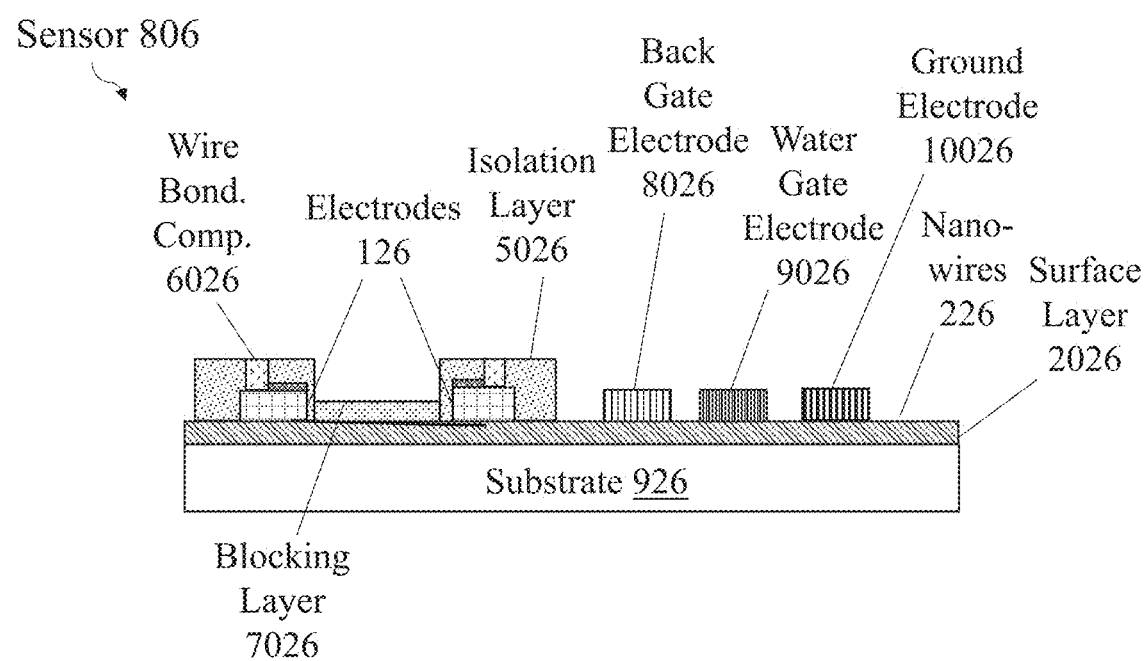
FIG. 8 shows one non-limiting embodiment of a sensor comprising a pair of electrodes and further comprising a back gate electrode, a water gate electrode, and a ground electrode, in accordance with some embodiments.

Further examples of sensors are illustrated in FIGS. 6-8. For instance, FIG. 6 shows one example of a nanowire sensor 606 having electrodes 122 and nanowires 222 disposed on surface layer 2022 of substrate 922. Sensor 606 further includes isolation layer 5022 (e.g., an electrically insulating layer) and wire bonding composition 6022. Isolation layer 5022 may be configured to isolate electrodes 122 from the surrounding environment. Wire bonding composition 6022, shown disposed on a portion of each member of the pair of electrodes 122, may be configured to facilitate electrical coupling between electrodes 122 and measurement device 104.

As shown in FIG. 6, wire bonding composition 6022 may be disposed directly on the electrode material in the electrode 122. It is also possible for the wire bonding composition to be disposed on the electrodes in a manner such that one or more intervening components are present between it and the electrode material. For instance, the wire bonding composition may be disposed on an electrically conductive material disposed on the electrode material, such as an electrically conductive material that facilitates bonding between the electrode material and the wire bonding composition. One example of an electrically conductive material suitable for this purpose is an alloy of titanium and gold. When the wire bonding composition is disposed directly on a portion of the electrode material in an electrode for which a passivating layer is disposed directly on a different portion thereof, the electrode material in the electrodes may be exposed for contact with the wire bonding composition by removing a portion of the passivating layer disposed thereon. This may be accomplished by, for instance, employing a photolithography technique described elsewhere herein.

In some embodiments, the surface chemistry of one or more components of sensor 606 may be altered to promote a desirable interaction with one or more analytes of interest. For instance, one or more types of molecules may be bound to the surfaces of nanowires 222. Such molecules may include those which are configured to bind with an analyte of interest (e.g., they may comprise antibodies for an antigen of interest). Molecules of interest may be bound to the nanowires by covalent attachment. In some embodiments, covalent attachment of molecules of interest to the nanowires may be facilitated by the use of silane derivatives. A silane derivative comprising a functional group suitable for bonding with the molecule of interest (e.g., an amino group, such as a primary amino group, an aldehyde group, an epoxy group) may be covalently attached to the nanowires. Then, the molecule(s) of interest may, after optionally being activated to facilitate bonding with the silane derivative, allowed to react with the silane derivative to form a covalent bond therewith. In some embodiments, it may be advantageous to alter the surface chemistry of the plurality of nanowires as one of the later steps during sensor fabrication and/or after steps during which the molecule(s) of interest may be degraded (e.g., after any photolithography steps, after any etching steps).

In some embodiments, a blocking layer may be formed on one or more components of sensor 606. The blocking layer may be positioned between these component(s) and an environment external to the sensor. In some embodiments, a blocking layer mediates interactions between one or more components of an environment external to the sensor (e.g., one or more samples to be analyzed and/or one or more components thereof, such as one or more analytes therein). For instance, a blocking layer may reduce non-specific interactions of sample(s) and/or component(s) therein with one or more components of the sensor (e.g., with a plurality of nanowires therein). Blocking layers suitable for this purpose may be formed from and/or comprise materials that do not bind readily with sample components (e.g., proteins) other than the analyte(s) of interest. As another example, a blocking layer may reduce electrostatic charge screening by a sample to be analyzed with one or more components of the sensor (e.g., with a plurality of nanowires therein).

A blocking layer may be introduced to a sensor by a variety of suitable processes. One example of a suitable process comprises dispensing a solution comprising the components of the blocking layer on the sensor and/or one or more components thereof and then incubating the sensor on which the solution is disposed to allow for bonding between the components of the blocking layer and the sensor and/or component(s) thereof.

When present, a blocking layer may be disposed on one or more discrete portions of the sensor or may form a coating that covers a significant fraction of the sensor (e.g., it may cover all, or a majority, of the portions of the sensor not in electrical communication with an environment external thereto). FIG. 7 shows one example of sensor 706, which further includes blocking layer 7024 that is disposed over nanowires 224, placing electrodes 124 in electrical communication, but absent from other portions of the sensor.

In some embodiments, electrodes may be positioned in other locations of the sensor than as described elsewhere herein in connection with FIGS. 6-7. By way of example, a sensor may further comprise a back gate electrode, a water gate electrode, and/or a ground electrode. These electrode(s), when present, may be formed by photolithography processes (e.g., as described elsewhere herein). They may be performed in a single step or may be fabricated by separate steps. The steps employed to form these electrode(s) may be performed at any suitable time. In some embodiments, one or more of these electrodes may be formed concurrently with the formation of the pair(s) of electrodes. For instance, a photolithographic process employed to form a pair of electrodes as described elsewhere herein may also comprise the formation of one or more further electrodes by also comprising removal of the photoresist from the location at which these electrode(s) are to be formed concurrently with removal of the photoresist from the location at which the pair of electrodes is to be formed and by also comprising deposition of the material forming these electrode(s) on the portion(s) of the substrate exposed by this process concurrently with deposition of the material forming the pair of electrodes.

FIG. 8 shows one non-limiting embodiment of sensor 806 including electrodes 126 as well as back gate electrode 8026, water gate electrode 9026, and ground electrode 10026.

Such additional electrodes, when present, may be directly exposed to an environment external to the sensor and/or may lack passivating layers and/or electrically insulating layers disposed thereon. In other embodiments, one or more passivating layers and/or electrically insulating layers may be positioned between one or more of these electrodes and an environment external thereto.

In some embodiments, a back gate electrode, a water gate electrode, and/or a ground electrode may be disposed on the substrate (e.g., substrate 926) such that it is in direct contact with the material forming the bulk thereof (e.g., instead of the surface layer). By way of example, in some embodiments, an electrode (e.g., a back gate electrode) is deposited onto a portion of the substrate from which the surface layer has been etched. Without wishing to be bound by any particular theory, it is believed that it may be advantageous for back gate electrodes to be disposed on the substrate such that they are in direct contact with the material forming the bulk thereof. It is believed that this arrangement may enhance the consistency of the gating provided by the back gate electrode, may allow for dry gating of the plurality of nanowires, and/or may provide a facile way to ground the bulk substrate.

Figure 3:
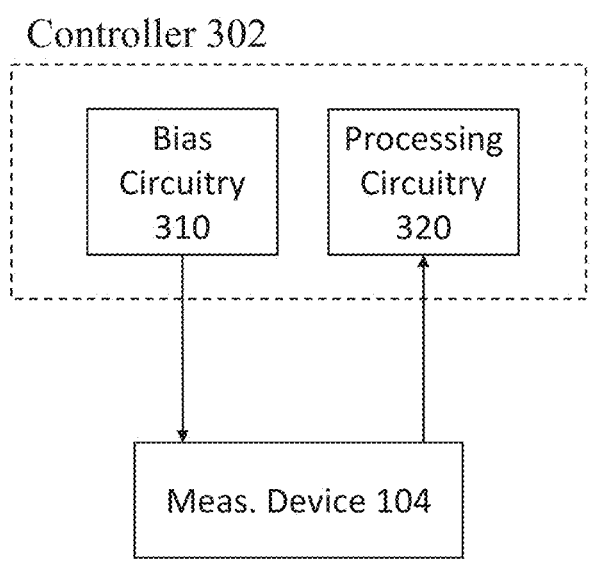
FIG. 3 shows an exemplary controller that may be included in the system of FIG. 1, in accordance with some embodiments.

Returning to system 100, FIG. 3 shows an exemplary controller 302 that may be included in system 100, in accordance with some embodiments. Controller 302 is shown including bias circuitry 310 and processing circuitry 320. Bias circuitry 310 may be configured to provide one or more bias signals to measurement device 104 for sensing electrical characteristics of a sensor. Processing circuitry 320 may be configured to receive a signal from measurement device 104 indicative of the electrical characteristics and to determine the electrical characteristics from the received signal. In some embodiments, processing circuitry 320 may be configured to set the bias signal(s) bias circuitry 310 is configured to provide, such as by providing a control signal to bias circuitry 310 indicative of the bias signal(s) to be generated by bias circuitry 310. In some embodiments, processing circuitry 320 may be configured to adjust the bias signal(s) to be generated by bias circuitry 310 using feedback received via measurement device 104 and/or bias circuitry 310.

In some embodiments, bias circuitry 310 may include one or more alternating current (AC) and/or direct current (DC) voltage sources configured to generate the bias signal(s). In some embodiments, bias circuitry 310 may include a battery and/or a voltage regulator configured to generate a DC voltage as a bias signal. For example, bias circuitry 310 may provide the DC voltage directly to measurement device 104. Alternatively or additionally, bias circuitry 310 may include modulation circuitry configured to generate an AC waveform using the DC voltage, such as a square and/or ramp wave. In some embodiments, bias circuitry may include an AC voltage source, such as a local oscillator configured to generate an AC waveform as a bias signal. For example, the AC waveform may be generated directly from the output of the local oscillator, or by mixing, filtering, integrating, or otherwise conditioning the output of the local oscillator. In some embodiments, bias circuitry 310 may be configured to generate an AC signal having a frequency between 0.1 Hz and 1 kHz. In some embodiments, bias circuitry 310 may be configured to generate an AC signal having a frequency between 500 Hz and 700 Hz. In some embodiments, bias circuitry 310 may be configured to generate an AC signal having a frequency of 600 Hz.

In some embodiments, bias circuitry 310 may include digital to analog conversion (DAC) circuitry and/or amplification circuitry. For instance, bias circuitry 310 may be configured to generate a digital AC waveform (e.g., square wave, etc.) and provide the AC waveform to measurement device 104 as an analog AC waveform (e.g., sine and/or triangle wave, etc.). Alternatively or additionally, bias circuitry 310 may be configured to generate the bias signal at a low voltage level (e.g., on the order of millivolts) and amplify the bias signal before providing the amplified bias signal to measurement device 104.

In some embodiments, processing circuitry 320 may be configured to determine the electrical characteristics of the sensor based on a signal received from measurement device 104. For example, the signal may be indicative of a current passing through the sensor, and processing circuitry 320 may be configured to determine the level of current passing through the sensor. Alternatively or additionally, processing circuitry 320 may be configured to determine the impedance of the sensor, such as using the determined level of current. For instance, may be configured to divide the voltage applied to the sensor by the determined level of current. For example, processing circuitry 320 may be configured to store a value of the voltage applied to the sensor (e.g., in a memory, register, etc.), and/or may calculate the value using settings provided to bias circuitry 310 for generating the bias signal(s). In some embodiments, processing circuitry 320 may include one or more processors (e.g., microprocessors, reduced instruction set processors, etc.) and/or digital logic circuitry (e.g., field programmable gate arrays, application specific integrated circuits, etc.) configured to determine the electrical characteristics, such as using stored instructions and/or other values in a memory, registers, latches, flip flops, and/or other storage media.

In some embodiments, processing circuitry 320 may include analog to digital conversion (ADC) circuitry and/or amplification circuitry. For instance, processing circuitry 320 may be configured to receive the signal indicating the electrical characteristics from measurement device 104 as an analog signal, whereas processing circuitry 320 may be configured to determine the electrical characteristics in the digital domain, such as using processor(s) and/or digital logic circuitry of processing circuitry 320. Alternatively or additionally, amplification circuitry of processing circuitry 320 may be configured to amplify the signal received from measurement device 104 to a voltage level suitable for determining the electrical characteristics.

In some embodiments having multiple controllers, a first controller may include bias circuitry 310 and a second controller may include processing circuitry 320. The first controller may include some processing circuitry as well, such as to set the bias signal(s) to be generated by bias circuitry 310. In some embodiments, bias circuitry 310 may be contained in a first integrated circuit package and processing circuitry 320 may be contained in a second integrated circuit package, for example, with the two integrated circuit packages disposed on a same PCB. In some embodiments, bias circuitry 310 and processing circuitry 320 may be contained in a single integrated circuit package.

The inventors have developed measurement devices configured to reduce and/or mitigate the impact of at least some electromagnetic noise in signals received via a sensor, thus improving the sensitivity of systems configured for sensing electrical characteristics of a sensor. In some aspects, the inventors recognized that the sensitivity of a measurement device may be degraded by electromagnetic noise generated in the system, such as in the sensor, the components of the system coupled to the measurement device, and even in the measurement device itself. In one example, amplifiers of the measurement device configured for coupling to the sensor may generate input-referred noise, such as current noise, that may be superimposed over signals received via the sensor. As a result, signals from the sensor should have sufficient signal power enough to overcome the noise generated by the amplifiers, thus impacting the ability of the measurement device to sense electrical characteristics of the sensor, and thereby decreasing the sensitivity of the system. While the level of noise generated in the amplifiers might be of a tolerable level for some applications, such as applications in which a current sensing path as a relatively low impedance (e.g., 1Ω) and the signals to be sensed are relatively large (e.g., on the order of µA, etc.).

Similarly, when the impedance of the current sensing path includes capacitance, the capacitance has little to no impact when the sensor is biased with a DC signal and the signal from the sensor indicating the electrical characteristics is at least substantially DC. However, when the impedance of the current sensing path is relatively high (e.g., 0.5 M Ω, 50 M Ω, 75 M Ω, 100 M Ω, or higher), and/or when the signals to be sensed are much smaller (e.g., on the order of pA), the otherwise tolerable level of noise has a much higher impact. Likewise, when an AC signal biases the sensor and the signal from the sensor indicating the electrical characteristics is correspondingly AC, the impact of even relatively small parasitic capacitances (e.g., on the order of pF) can add to the level of noise in the sensed signals.

Measurement devices described herein may address the above problems at least in part by arranging and/or interconnecting components of the measurement devices in a manner that reduces and/or mitigates the impact of electromagnetic noise generated by the components of the measurement device, the sensor, and/or other system components.

Figure 4:
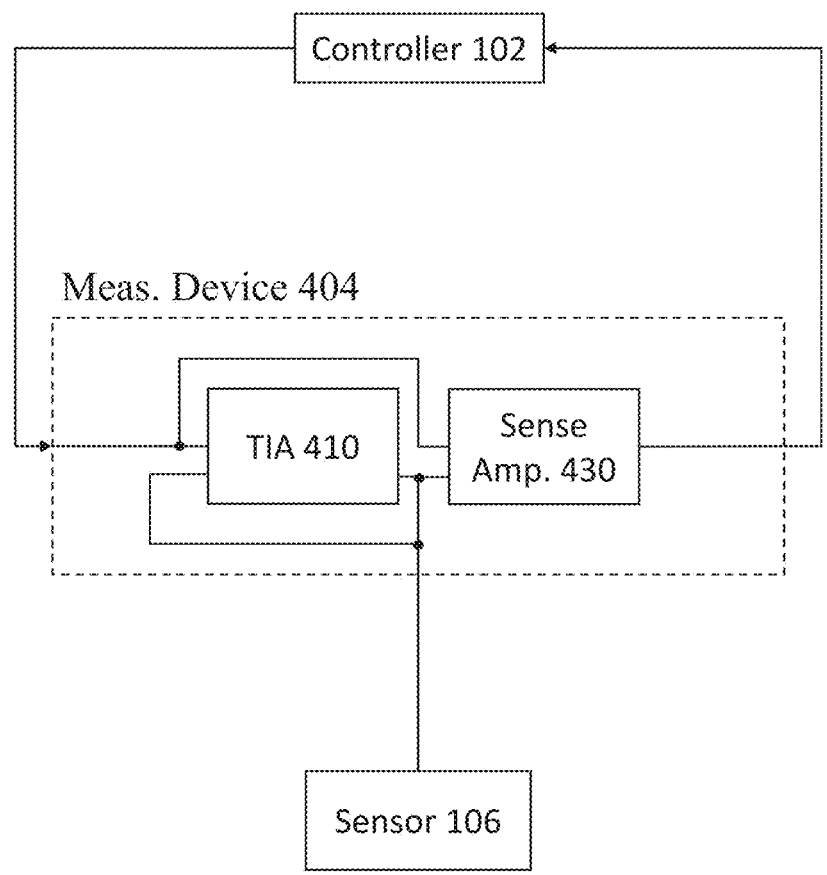
FIG. 4 shows an exemplary measurement device that may be included in the system of FIG. 1, in accordance with some embodiments.

FIG. 4 shows exemplary measurement device 404 that may be included in system 100, in accordance with some embodiments. Measurement device 404 is shown including transimpedance amplifier (TIA) 410 and sense amplifier 430. A first input of TIA 410 is coupled to an output of controller 102 and also to a first input of sense amplifier 430. A second input of TIA 410 is coupled to an output of TIA 410, sensor 106, and to a second input of sense amplifier 430. An output of sense amplifier 430 is coupled to controller 102. In some embodiments, TIA 410 may be configured to receive one or more bias signals from bias circuitry of controller 102 and to apply a bias voltage and/or current to sensor 106 using the bias signal(s). Sense amplifier 430 may be configured to receive a signal via TIA 410 and sensor 106 and to generate a signal indicative of electrical characteristics of sensor 106 at the output coupled to controller 102.

The inventors recognized that interference, such as current noise and distortion generated in the sense amplifier may interfere with signals received from the sensor. For instance, when input terminals of the sense amplifier are coupled across a sense resistor that receives a current from the sensor, current noise generated in the sense amplifier may add to the current from the sensor as noise. Moreover, parasitic capacitances in components of the system may add non-linear impedance to the sense path distorting the received signals. One technique the inventors developed to address this problem is to couple the inputs of sense amplifier 430 to the inputs of TIA 410 such that current noise from sense amplifier 430 does not flow in a loop between its inputs. Additionally, parasitic capacitances in sense amplifier 430 are separated from the sense path to limit the amount of distortion added to the sensed signals. As a result, the configuration of measurement device 404 reduces the impact of current noise generated in sense amplifier 430 on signals received from sensor 106. In some embodiments, measurement device 404 may be configured to provide an AC voltage to sensor 106, as the impact of distortion from the parasitic capacitances is largely mitigated. The illustrated configuration also facilitates grounding a terminal of sensor 106, thus providing improved protection against overvoltage events, as described herein.

It should be appreciated that amplifiers 410 and/or 430 may include multiple outputs, such as in embodiments in which amplifiers 410 and/or 430 are configured to generate and output differential signals. It should also be appreciated that, in some embodiments, measurement device 404 may be coupled to multiple terminals of sensor 106, such as in embodiments configured to apply a differential signal to sensor 106, and/or in embodiments configured to apply a ground reference to sensor 106 in addition to biasing sensor 106.

In some embodiments, TIA 410 may be contained in a single integrated circuit package. Alternatively or additionally, in some embodiments, sense amplifier 430 may be contained in a single integrated circuit package. In some embodiments, integrated circuit packages containing TIA 410 and sense amplifier 430, respectively, may be disposed on a same PCB. In some embodiments, TIA 410 and sense amplifier 430 may be contained in a same integrated circuit package. In some embodiments, components of TIA 410 and/or sense amplifier 430 may be discrete components, such as discrete field effect transistors (FETs).

Figure 5:
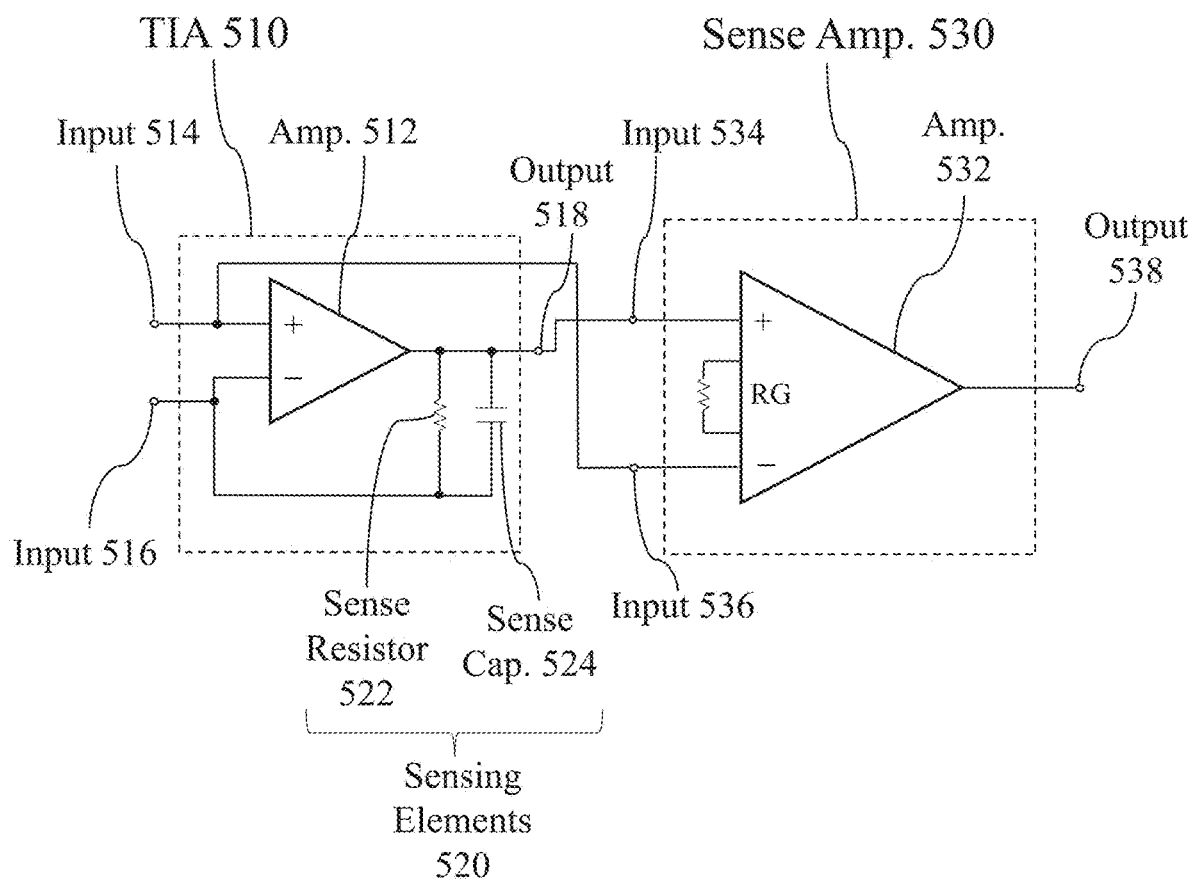
FIG. 5 shows a circuit diagram of exemplary components of the measurement device of FIG. 4, in accordance with some embodiments.

FIG. 5 shows a circuit diagram of exemplary TIA 510 and sense amplifier 530, which may be included in measurement device 404, in accordance with some embodiments. TIA 510 is shown including amplifier 512 and sensing elements 520, and sense amplifier 530 is shown including amplifier 532. Amplifier 512 of TIA 510 has first input 514, second input 516, and output 518. Amplifier 532 of sense amplifier 530 has first input 534 coupled to output 518 of amplifier 512, second input 536 coupled to first input 514 of amplifier 512, and output 538. Sensing elements 520 include sense resistor 522 and sense capacitor 524 coupled between second input 516 and output 518 of amplifier 512. In some embodiments, input 514 of amplifier 512 and/or output 538 of amplifier 532 may be configured for coupling to controller 102. For instance, in some embodiments, TIA 510, sense amplifier 530, and at least a portion of controller 104 may be disposed on a single PCB such that conductive traces on the PCB may couple TIA 510 and/or sense amplifier 530 to controller 104. Second input 516 of amplifier 512 may be configured for coupling to sensor 106. For instance, in some embodiments, second input 516 of amplifier 516 may be coupled to an electrical connector configured for removably coupling to a complementary electrical connector of sensor 106. In one example, the electrical connectors may be configured to repeatedly and/or non-permanently couple to and decouple from one another.

Amplifier 512 of TIA 510 may be configured to bias sensor 106. In some embodiments, amplifier 512 may include an integrated circuit, such as disposed within its own integrated circuit package. In some embodiments, sensing elements 520 may be disposed in a same integrated circuit package as amplifier 512. In some embodiments, components of amplifier 512 may be discrete, such as including one or more discrete FETs. First input 514 of amplifier 512 may be configured to receive a bias signal from controller 102. Second input 516 may be configured to bias sensor 106 using the bias signal. For instance, as shown, output 518 of amplifier 512 is coupled to second input 516 via sensing elements 520, such that amplifier 512 may be configured to pull the voltage at second input 516 to the voltage at first input 514. As a result, amplifier 512 may apply a voltage to sensor 106 that is substantially equal to the voltage of the received bias signal.

Sensing elements 520 may be configured to receive a signal from sensor 106 via second input 516 and generate a sense voltage. For instance, second input 516 may receive a current flowing through sensor 106 in response to the bias voltage being applied to sensor 106, and the received current may generate the sense voltage across sensing elements 520. Thus, second input 516 of amplifier 512 may serve as an output of TIA 510 configured to generate a sense voltage indicative of the current through the sensor.

In some embodiments, sensing elements 520 may be configured to provide a transimpedance gain of at least 1μ V/pA, such as 5μ V/pA or higher at DC and/or at a frequency of the applied bias signal (e.g., between 0.1 Hz and 1 kHz, between 500 Hz and 700 Hz, at 600 Hz etc.). In accordance with various embodiments, sense resistor 522 may have a resistance between 0.1 M Ω and 75 M Ω, such as between 0.25 M Ω and 50 M Ω, between 1 M Ω and 25 M Ω, between 25 M Ω and 50 M Ω, and/or the like. It should be appreciated that other impedance elements may be included and/or used in place of sense resistor 522 and/or sense capacitor 524.

Amplifier 532 of sense amplifier 530 may be configured to receive the sense voltage via TIA 410 and sensor 106. In some embodiments, sense amplifier 530 may include an amplifier, such as an operational amplifier, instrumentation amplifier, and/or difference amplifier. In some embodiments, components of amplifier 532 may be discrete, such as including discrete FETs. First input 534 and second input 536 of amplifier 532 may be configured to receive the sense voltage generated by sensing elements 520 in response to receiving the current from sensor 106. For instance, first input 534 is coupled to output 518 of amplifier 512 and sensing elements 520, and second input 536 is coupled to input 514 of amplifier 512. As shown in FIG. 5, second input 516 is configured to provide substantially the same voltage to sensor 106 as received from controller 102 at first input 514. Accordingly, second input 536 of amplifier 532 receives substantially the same voltage as if second input 536 were coupled to second input 516 and sensing elements 520. Moreover, because second input 536 is coupled to first input 514, the impact of current noise (e.g., input bias current) generated in amplifier 532 on signals received via sensor 106 may be mitigated as described herein. Amplifier 530 may be configured to generate a signal indicative of the electrical characteristics at output 538 for providing to controller 102. In some embodiments, amplifier 532 may be configured to amplify the signals received at inputs 534 and 536 by a set gain parameter to generate an amplified signal at output 538. For instance, as shown in FIG. 5, the gain of amplifier 532 may be set by coupling a resistor between gain setting inputs RG.

It should be appreciated that, in some embodiments, TIA 510 may be configured to apply the same bias signal received from controller 102 to a terminal of the sensor. Alternatively, a voltage divider and/or diode may be coupled between second input 516 and output 518 such that a voltage different from the voltage of the bias signal may be applied to the sensor. For example, the applied voltage may have a voltage offset and/or may be proportional to the voltage of the bias signal.

It should be appreciated that, in some embodiments, TIA 510 and/or sense amplifier 530 and controller 102 may be positioned on different PCBs and/or in different enclosures. Alternatively or additionally, in some embodiments, TIA 510 and/or sense amplifier 530 may be coupled to controller 102 using one or more electrical connectors. Alternatively or additionally, in some embodiments, second input 516 may be coupled to sensor 106 by other means, such as conductive traces on one or more PCBs.

Figure 9:
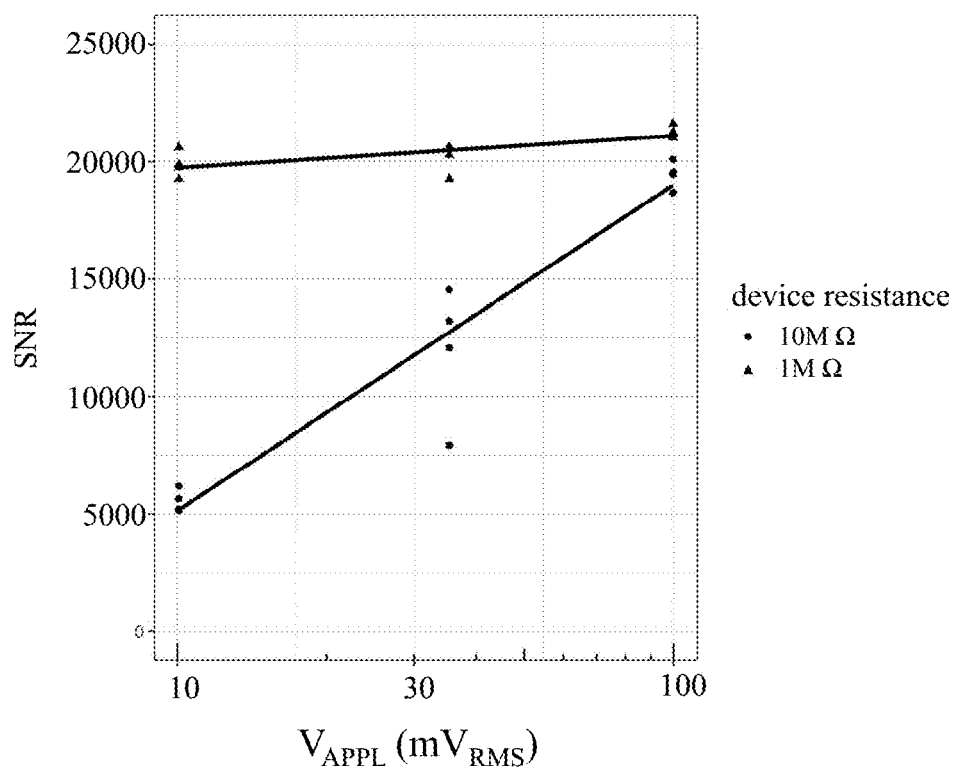
FIG. 9 shows a graph of signal-to-noise ratio (SNR) of a voltage at the output of a measurement device versus voltage applied by the measurement device across a sensor, in accordance with some embodiments.

FIG. 9 shows a graph 900 of SNR of a voltage at the output of a measurement device versus voltage $V_{APPL}$ applied by the measurement device across a sensor, in accordance with some embodiments. A measurement device, including components configured in the manner described herein in connection with FIG. 5, was placed in a system with a sensor configured in the manner described herein for sensor 206 in connection with FIG. 2. In order to evaluate noise intrinsic to the measurement system, the nanowire 220 in sensor 206 was modelled by a thin-film resistor with an indicated resistance value.

As shown in FIG. 9, the measurement device applied voltages $V_{APPL}$ between 10 $mV_{RMS}$ and 100 $mV_{RMS}$ to the sensor 206 (via input 516 of TIA 510). In response to applying the voltages $V_{APPL}$ to the sensor 206, the measurement device generated an output voltage (at the output 538 of the sense amplifier 530). The output voltage corresponded to a sensed resistance of the sensor 206 and included signal content and noise content, the signal content including voltage caused by the resistance of the sensor and the noise content including voltage caused by noise in the system.

The ratio of signal content to noise content in the output voltage was determined by converting the output voltage to a digital signal using 24-bit ADC circuitry and calculating an amplitude of the output voltage by executing a lock-in amplifier process on the digital signal using a processor. Once the output voltage amplitude was calculated, the noise content in the output voltage was determined by calculating the standard deviation of the signal. The signal content was calculated as a mean value of the signal. In a first set of measurements, labeled in FIG. 9 with circular dots (●), the nanowire 220 of the sensor 206 had an indicated resistance of 10 M Ω. In a second set of measurements, labeled in FIG. 9 with triangles (▲), the nanowire 220 had an indicated resistance of 1 M Ω.

As shown in FIG. 9, the measurement device achieved an SNR of over 20,000 for voltages $V_{APPL}$ between 10 $mV_{RMS}$ and 100 $mV_{RMS}$ applied to the sensor 206 having a resistance of 1 M Ω. The measurement device achieved an SNR of over 5,000 for voltages $V_{APPL}$ between 10 $mV_{RMS}$ and 100 $mV_{RMS}$ applied to the sensor 206 having a resistance of 10 M Ω, including an SNR over 10,000 for voltages $V_{APPL}$ between 30 $mV_{RMS}$ and 100 $mV_{RMS}$ and an SNR over 20,000 for a voltage $V_{APPL}$ of 100 $mV_{RMS}$.

While several embodiments of the present technology have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present application.

For example, while measurement devices having analog components have been described herein, it should be appreciated that digital components may be used as alternative or additional components of measurement devices described herein. Also, while discrete FET components of amplifiers have been described herein, such discrete components may alternatively or additionally include bipolar components and/or high electron mobility transistors, in accordance with various embodiments. Also, while nanowire sensors are described as one example of a sensor that may be used in accordance with the technology described herein, other sensors may be used such as nanotube sensors.

For example, in general, a plurality of nanowires comprises nanowires having a chemical composition that is desirable. By way of example, the nanowires may be formed from and/or comprise a material that is capable of being functionalized with one or more chemistries of interest (e.g., one or more chemistries having a desirable interaction with an analyte of interest and/or which can further react with a molecule having a desirable interaction with an analyte of interest). As another example, the nanowires may be formed from and/or comprise a material having a desirable electrical conductivity and/or equivalent surface potential (e.g., from a semiconductor, from a material that exhibits a change in electrical conductivity upon exposure to an analyte of interest, and/or from a material that exhibits a change in equivalent surface potential upon exposure to an analyte of interest). Non-limiting examples of materials having this property include selected elements (e.g., silicon), ceramics (e.g., gallium nitride, gallium arsenide, indium oxide, indium phosphide, molybdenum disulfide, tungsten disulfide), polymers (e.g., semiconducting polymers), one-dimensional materials (e.g., carbon nanotubes, one-dimensional materials comprising one or more of the above-referenced materials), and two-dimensional materials (e.g., graphene, two-dimensional materials comprising one or more of the above-referenced materials). In some embodiments, the nanowires are formed from and/or comprise one or more of the above-referenced materials in single-crystalline form (e.g., single-crystalline silicon). Additional characteristics of nanowires and sensors are provided in U.S. Application No. 62/953,140 filed Dec. 23, 2019, entitled Sensor System and Methods, which is incorporated herein by reference in its entirety for all purposes.

More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the technology described herein. It is, therefore, to be understood that the foregoing embodiments are presented by way of example only and that, within the scope of the appended claims and equivalents thereto, the aspects of the technology may be practiced otherwise than as specifically described and claimed. The present application is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present application.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A system comprising:
a sensor configured to generate an impedance greater than 0.5 megaohms (M Ω) when at least some analytes are disposed proximate the sensor; and
circuitry configured to provide an alternating current (AC) voltage to the sensor and sense electrical characteristics of the sensor in response to the AC voltage, the circuitry comprising:
a sense resistor coupled to the sensor;
a first amplifier having a first input, a second input, and an output, with the sense resistor coupled between the second input and the output; and
a second amplifier comprising:
a first input coupled to the output of the first amplifier;
a second input coupled to the first input of the first amplifier; and
an output configured to provide a voltage indicative of the electrical characteristics of the sensor,
wherein the first amplifier is configured to provide the AC voltage to the sensor via the second input.

2. The system of claim 1, wherein the electrical characteristics include a conductance of the sensor.

3. The system of claim 2, wherein the sensor is a nanowire sensor, and wherein the nanowire sensor is configured such that the conductance indicates a presence of one or more analytes at a surface of the nanowire sensor.

4. The system of claim 3, wherein the surface of the nanowire sensor comprises a binding entity for a biomarker for brain injury.

5. The system of claim 3, wherein the surface of the nanowire sensor comprises a binding entity for a biomarker for one or more infectious disease agents.

6. The system of claim 1, further comprising a transimpedance amplifier (TIA) including the sense resistor and the first amplifier, wherein the TIA is configured to generate a sense voltage indicative of a current flowing through the sensor.

7. The system of claim 6, further comprising an integrated circuit package, wherein the TIA is contained in the integrated circuit package, the TIA comprises a plurality of discrete components, and the plurality of discrete components comprises a field-effect transistor (FET).

8. A system, comprising:
a sensor configured to generate an impedance greater than 0.5 megaohms (M Ω) when at least some analytes are disposed proximate the sensor; and
circuitry configured to provide an alternating current (AC) voltage to the sensor and sense electrical characteristics of the sensor in response to the AC voltage, the circuitry comprising:
a sense amplifier comprising a first input and an output, the sense amplifier configured to generate a voltage indicative of the electrical characteristics at the output; and
a transimpedance amplifier (TIA) comprising an amplifier, the amplifier comprising:
a first input coupled to the first input of the sense amplifier; and
a second input coupled to, and configured to provide the AC voltage to, the sensor.

9. The system of claim 8, wherein the electrical characteristics include a conductance of the sensor.

10. The system of claim 9, wherein the sensor comprises a nanowire sensor, and wherein the nanowire sensor is configured such that the conductance indicates a presence of one or more analytes at a surface of the nanowire sensor.

11. The system of claim 10, wherein the surface of the nanowire sensor comprises a binding entity for a biomarker.

12. The system of claim 11, wherein the biomarker is a biomarker for brain injury.

13. The system of claim 11, wherein the biomarker is a biomarker for one or more infectious disease agents.

14. The system of claim 8, wherein:
the amplifier of the TIA further comprises an output electrically coupled to a second input of the sense amplifier;
the amplifier of the TIA is configured to generate a sense voltage at the output of the amplifier of the TIA that is indicative of a current through the sensor; and
the TIA further comprises a sense resistor electrically coupled between the first input of the amplifier of the TIA and the output of the amplifier of the TIA and configured to generate the sense voltage when the current flows through the sense resistor.

15. The system of claim 14, wherein the amplifier of the TIA is further configured to receive an input voltage signal at the first input of the amplifier of the TIA and to apply the input voltage signal to the sensor via the second input of the amplifier of the TIA.

16. A system for sensing electrical characteristics of a sensor, comprising:
a sensor comprising a first electrode and a second electrode, the sensor configured to generate an impedance between the first electrode and the second electrode that is greater than 0.5 M Ω when at least some analytes are disposed proximate the sensor;
a transimpedance amplifier (TIA) comprising an amplifier configured to provide an alternating current (AC) voltage across the first electrode and the second electrode of the sensor; and
a sense amplifier configured to generate a voltage indicative of the electrical characteristics of the sensor responsive to detecting a current flowing between the sensor and ground, the electrical characteristics of the sensor comprising the impedance between the first electrode and the second electrode, and the impedance being indicated by a relationship between the AC voltage and the current flowing between the sensor and ground,
wherein the current flowing between the sensor and ground is responsive to the sensor receiving the AC voltage from the amplifier of the TIA while at least some analytes are disposed proximate the sensor.

17. The system of claim 16, wherein the amplifier of the TIA is configured to receive the AC voltage from an AC voltage source having a frequency between 500 Hz and 700 Hz.

18. The system of claim 16, wherein the electrical characteristics include a conductance of the sensor.

19. The system of claim 18, wherein the sensor comprises a nanowire sensor, and wherein the nanowire sensor is configured such that the conductance indicates a presence of one or more analytes at a surface of the nanowire sensor.

20. The system of claim 19, wherein the nanowire sensor is configured to generate an impedance greater than 0.5 M Ω when at least some analytes are disposed at the surface of the nanowire sensor.

21. The system of claim 19, wherein the surface of the nanowire sensor comprises a binding entity for a biomarker for brain injury.

22. The system of claim 19, wherein the surface of the nanowire sensor comprises a binding entity for a biomarker for one or more infectious disease agents.

23. The system of claim 16, wherein an input of the amplifier of the TIA is configured to receive the current and an output of the amplifier of the TIA is configured to provide a sense voltage to the sense amplifier, and wherein the TIA further comprises a sense resistor configured to generate the sense voltage when the current flows through the sense resistor.

* * * * *